United States Patent
Biagini et al.

(10) Patent No.: US 6,844,478 B2
(45) Date of Patent: Jan. 18, 2005

(54) SUBSTITUTED POLYCYCLIC CYCLOPENTADIENES AND METHOD FOR THEIR PREPARATION

(75) Inventors: Paolo Biagini, Trecate (IT); Diego Vigliarolo, Rho (IT); Giampietro Borsotti, Novara (IT); Roberto Santi, Novara (IT)

(73) Assignee: Polimeri Europa S.p.A., Brindisi (IT)

( * ) Notice: Subject to any disclaimer, the term of this patent is extended or adjusted under 35 U.S.C. 154(b) by 100 days.

(21) Appl. No.: 10/240,279
(22) PCT Filed: Mar. 20, 2001
(86) PCT No.: PCT/EP01/03127
§ 371 (c)(1), (2), (4) Date: Sep. 30, 2002
(87) PCT Pub. No.: WO01/74745
PCT Pub. Date: Oct. 11, 2001

(65) Prior Publication Data
US 2003/0166800 A1 Sep. 4, 2003

(30) Foreign Application Priority Data
Mar. 31, 2000 (IT) .................. MI2000A0680

(51) Int. Cl.$^7$ ............................. C07C 13/547
(52) U.S. Cl. .............. 585/409; 585/408; 585/416; 585/411
(58) Field of Search ................. 585/408, 409, 585/411, 416

(56) References Cited

FOREIGN PATENT DOCUMENTS

EP 0 849 273 6/1998

OTHER PUBLICATIONS

Chemical Abstracts, vol. 97, No. 21 abstract No. 181816s Nov. 22, 1982.

*Primary Examiner*—Caixia Lu
(74) *Attorney, Agent, or Firm*—Oblon, Spivak, McClelland, Maier & Neustadt, P.C.

(57) ABSTRACT

New polycyclic cyclopentadiene compounds having the formula (II) wherein the various substituents and symbols $R_1$, $R_2$, $R_3$, $R_4$, $R_5$, $R_6$, $R_7$, $Z^1$ and $Z^2$ and "n" have the meaning specified in the description. These compounds can form metallocene complexes with transition metals, which have shown unusual properties in the (co)polymerization of ethylene and alpha-olefins in general

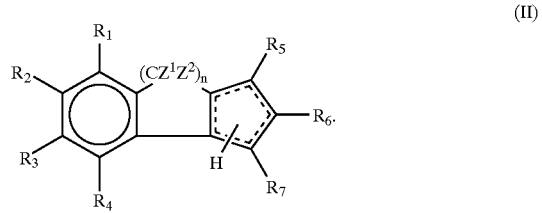

9 Claims, No Drawings

SUBSTITUTED POLYCYCLIC CYCLOPENTADIENES AND METHOD FOR THEIR PREPARATION

The present invention relates to compounds of the group of cyclopentadienes substituted to form polycyclic structures, as well as a process for their preparation.

More specifically, the present invention relates to new polycyclic cyclopentadienyl compounds which can be used, in the form of anions, as penta-hapto ($\eta^5$-) ligands coordinated to transition metals to form metallocenes.

The property of cyclopentadienyl compounds of easily forming an anion of an aromatic nature by the loss of a cationic fragment, usually an $H^+$ anion, is known. The capacity of these anions of coordinating themselves to metal cations by means of a multi-electronic complex bond to form complexes, called metallocenes, having an unusual relative stability with respect to the behaviour generally expected for organometallic compounds containing hydrocarbon anions, is also well known. These complexes may contain a single cyclopentadienyl ligand, or 2 and, in certain cases, even three ligands of this type. Cyclopentadienyl complexes of transition metals of Groups 3 to 6, and particularly of Group 4 of the periodic table, combined with aluminoxanes or particular salts of non-coordinating anions, are known to be capable of polymerizing α-olefins and have been widely used for this purpose in the recent past.

Cyclopentadienyl compounds comprise the di-unsaturated cyclic group with five carbon atoms having the following general formula (I):

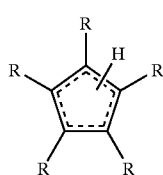

(I)

wherein the R groups represent general substituents, either the same or different.

In accordance with the present invention and in order to simplify the description and claims, the above formula (I) is used herein to synthetically represent one or more of the five possible mesomeric structures (Ia), (Ib), (Ic), (Id) and (Ie) indicated below, which, as is normally customary in organic chemistry, can represent a general poly-substituted cyclopentadienyl compound.

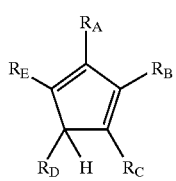

(Ia)

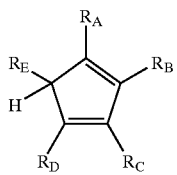

(Ib)

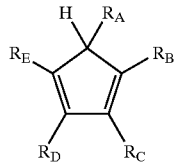

(Ic)

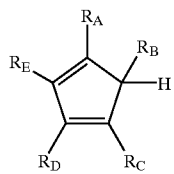

(Id)

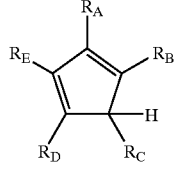

(Ie)

These can be converted to one another by the shifting, in the pentagonal cycle, of the two double bonds and the hydrogen atom linked to the sole saturated carbon atom, the various substituents of the cycle usually being hydrogen or linear or branched organic radicals, optionally substituted, which, in the more general version, can also form one or more covalent ligands with each other to obtain cyclic or polycyclic structures condensed with said cyclopentadienyl ring. For the purposes of the present invention, these structures (Ia), (Ib), (Ic), (Id) and (Ie) can be considered as being equivalent, as they are precursors of the same cyclopentadienyl anion. Consequently, unless otherwise specified, the scope of the present invention, with reference to the cyclopentadienyl compounds represented by structural formulae of the type (I), which form one of the objects thereof, comprises the five mesomeric structures defined above.

Substituted cyclopentadienyl hydrocarbon compounds consisting of saturated and unsaturated rings condensed on the cyclopentadienyl ring are known in the art, and some of them are commercial products, such as, for example, indene, tetrahydroindene, fluorene, azulene, 1,2-benzofluorene. Other bicyclic compounds comprising a cyclopentadienyl ring are described in European patent application EP-A 760,355, whereas European patent application EP-A 849,273 describes metallocene complexes with these ligands, suitable for polymerizing olefins.

The positive effect of saturated cycles condensed with cyclopentadienyl rings in the polymerization catalysis of olefins, using metallocenes of zirconium and titanium, has also been acknowledged, especially with respect to the activity and incorporation of co-monomers in the co-polymerization of ethylene with α-olefins, as described for example in European patent application EP-A 849,273.

In spite of the encouraging results obtained so far in this field, there is still the request for continuous improvements in polymerization catalysts and in the quality and versatility of poly-α-olefins obtained therewith. The request for elastomeric polymers of ethylene with a high content of unsaturations suitable for a rapid vulcanization, has stimulated research relating to catalysts capable of increasing the quantity of non-conjugated dienes incorporated in the ethylene copolymer with respect to what is so far possible, without causing a significant decrease in the average molecular weight of the product obtained. However it is desirable to have catalysts capable of producing polyolefins with an increased molecular weight for high yield processes operating at temperatures higher than 100° C. Finally, further improvements are required in the steric control of the stereospecific polymerization of α-olefins to give polymers with a high tacticity by means of metallocene catalysts of the so-called "bridged" type, having structures which are becoming more and more sophisticated and selective.

In the never-ending attempt to respond to the above demands with innovative processes and materials, the Applicant has now found a new group of polycyclic cyclopentadienyl compounds, suitable for use in the preparation of catalysts which represent a definite progress in providing a solution to the above problems.

A first object of the present invention therefore relates to a polycyclic cyclopentadienyl compound having the following formula (II):

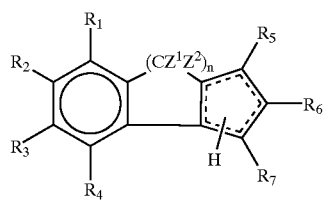

(II)

wherein: each $R_1$, $R_2$, $R_3$, $R_4$, $R_5$, $R_6$, $R_7$, $Z^1$ and $Z^2$ is independently hydrogen or an organic substituent having from 1 to 10 carbon atoms, preferably selected from hydrocarbon radicals having from 1 to 8 carbon atoms, more preferably $C_1$–$C_6$ alkyl, linear or branched, and in addition, any one of said R or Z groups, preferably one of the groups selected from $Z^1$, $Z^2$, $R_5$, $R_6$, or $R_7$, can be a divalent organic group further bound to another organic group having from 5 to 20 carbon atoms and comprising a cyclopentadienyl group, and "n" has any of the integer values from 1 to 10 extremes included, and preferably ranges from 1 to 3.

As already specified above, in the above formula (II), the cyclopentadienyl group is conventionally represented by a structure which comprises all the mesomeric forms obtainable by shifting the double bonds and the hydrogen atom in the cycle as required by the valency regulations. This shifting is not only formal, but can be easily obtained in practice by forming a cyclopentadienyl anion of any compound having formula (II), for example by treatment with lithium butyl, and by subsequently acidifying to obtain a mixture of all possible five isomers, said mixture being also included in the scope of the present invention.

In a preferred embodiment, the present invention relates to compounds having formula (II) wherein all the R and Z groups are hydrogen. In another preferred embodiment, $Z^1$ and $Z^2$ are hydrogen and only two of the groups $R_1$, $R_2$, $R_3$, $R_4$ are linear or branched alkyl with from 1 to 4 carbon atoms.

According to other particular forms of the present invention, one of the $R_5$, $R_6$ or $R_7$ groups is methyl or ethyl, more preferably methyl. In another preferred embodiment, $R_1$ and $R_3$ are methyl, and "n" is 2 or 3.

According to a particular embodiment of the present invention, one of the $R_5$, $R_6$, or $R_7$ groups, preferably $R_5$ or $R_7$, is a divalent hydrocarbon or silane group having from 2 to 6 carbon atoms, further linked to a second cyclopentadienyl group having from 5 to 20 carbon atoms, preferably selected from cyclopentadienyl, indenyl, fluorenyl and homologous groups thereof, in particular linked to said $R_5$, $R_6$, or $R_7$ group by means of a carbon atom of the cyclopentadienyl ring.

Non-limiting examples of compounds having formula (II) are those represented by the following formulae, which for the purposes of simplicity, are not numbered:

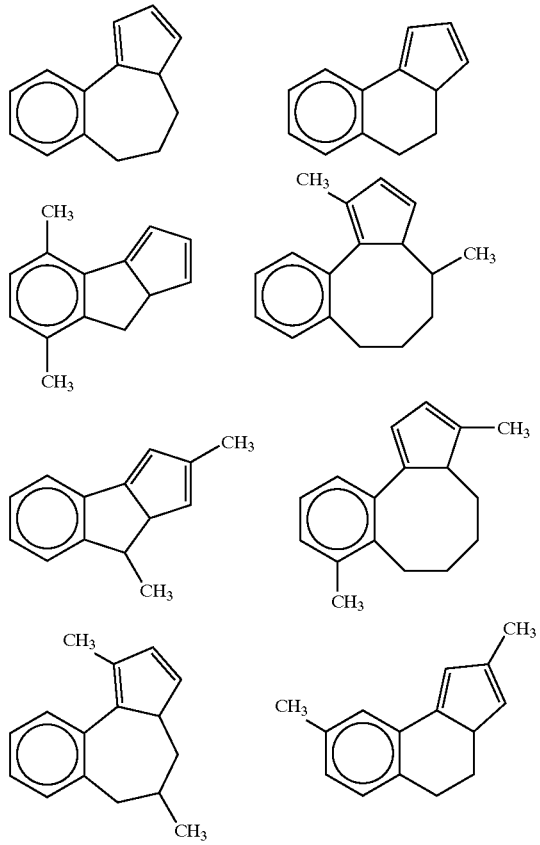

The polycyclic cyclopentadienyl compounds according to the present invention are relatively stable compounds, they can be exposed to air, even if it is not convenient to keep them for long periods due to the possibility of the formation of the corresponding dimeric products, according to the well known Diels-Alder reaction. For this reason, when there is the possible necessity of keeping these products for some time, it is preferable to transform them into one of the corresponding salts of alkaline or earth-alkaline metals, which, although being sensitive to oxygen and humidity present in the air, do not undergo any chemical alterations if kept in an inert atmosphere.

These polycyclic compounds, although new, can be prepared by adapting known techniques of organic chemistry for the purpose, by analogy with synthetic methods of compounds and organic structures already known or similar, such as, for example, the synthesis method described in the European patent application cited above EP-A 760,355. The Applicant however has developed an original synthetic method, by modifying or combining known techniques, which allow these compounds to be obtained with a good yield in a limited number of steps.

A second object of the present invention therefore relates to a method for the preparation of the polycyclic cyclopentadienyl compounds having formula (II) starting from a benzoketone having the following general formula (III):

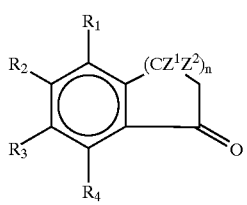

(III)

wherein the various symbols have the same meaning defined above, both in the general and in the preferred forms, with reference to the cyclopentadienyl compounds having formula (II), comprising the following steps in succession:

i) forming the anion of said benzoketone having formula (III) by the extraction of a hydrogen ion in alpha position with respect to the carbonyl, by means of reaction with a hydride or an alkyl of an alkaline metal, ii) reacting the anion formed in step (i) with an alkyl carbonate having the formula $OC(OR_8)$ wherein $R_8$ is linear or branched alkyl having from 1 to 6 carbon atoms, to obtain the benzoketoester having the following formula (IV):

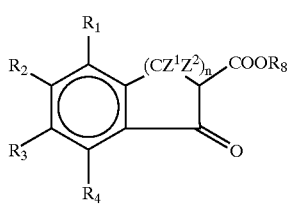

(IV)

iii) forming the anion of said benzoketoester having formula (IV) by reaction with a sufficiently strong organic base, for example a hydride, an alkoxide or an alkyl of an alkaline metal, and reacting said anion with a propargyl halide having the following formula (V)

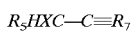

$R_5HXC-C\equiv R_7$ (V)

wherein $R_5$ and $R_7$ have the same meaning as the corresponding symbols of formula (II) and X is halogen excluding fluorine, preferably chlorine or bromine, to obtain at the end the following compound having formula (VI)

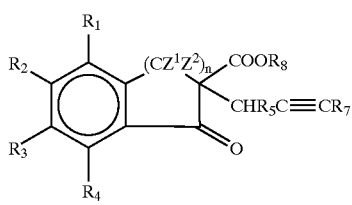

(VI)

iv) hydrating said compound having formula (VI) with one of the known methods for transforming the acetylene group into a ketone group, for example by contact and reaction in a mixture with mercury oxide, etherate boron trifluoride, trichloroacetic acid in methanol as solvent, and subsequent hydrolysis, in order to obtain the following compound having formula (VII):

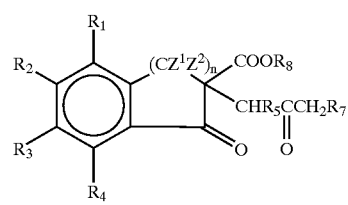

(VII)

v) cyclizing said compound having formula (VII) by self-condensation in a strongly basic environment by KOH or NaOH, at temperatures preferably ranging from 20 to 100° C., in order to obtain the following unsaturated cyclic ketone having formula (VIII):

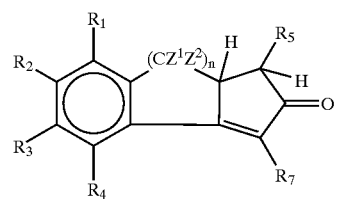

(VIII)

vi) reducing said unsaturated cyclic ketone having formula (VIII) using one of the known methods, for example by reaction with lithium aluminum hydride, to obtain the desired polycyclic cyclopentadienyl compound having formula (IX), corresponding to the compound having formula (II) with $R_6$ equal to hydrogen:

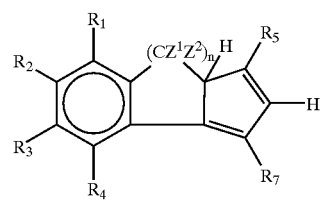

(IX)

or by means of reaction with a suitable reactive metal alkyl comprising the $R_6$ group, for example lithium alkyl, a Grignard reagent, a magnesium dialkyl, an aluminum trialkyl etc., to obtain the desired compound having general formula (II) object of the present invention.

The above polycyclic cyclopentadienyl compounds can be used for the formation of organometallic complexes of transition metals, particularly of group 4 of the periodic table of elements, which can be advantageously used as catalysts in various synthetic processes, such as for example, hydrogenation, oxidation and polymerization of olefins.

A further object of the present invention therefore relates to saline (ionic) compounds comprising at least one polycyclic cyclopentadienyl anion formally deriving from any of the previous compounds having formula (II) by the extraction of an $H^+$ acid anion from the cyclopentadienyl ring, and also metal complexes comprising at least one of said cyclopentadienyl anions coordinated to a transition metal by means of covalent bonds of the $\pi$ type. In particular, an object of the present invention relates to an organometallic compound having the following general formula (X):

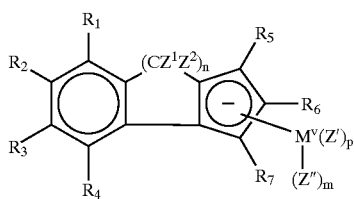

(X)

wherein:
- each $R_1, R_2, R_3, R_4, R_5, R_6, R_7, Z^1$ and $Z^2$ group, and also "n", has the same meaning, both general and preferred, as the corresponding symbol in formula (II) above;
- $M^v$ represents any metal of the periodic table of elements having an oxidation state (or valence) "v" greater than zero;
- each Z' is independently a group of an anionic nature bound to the metal $M^v$ as anion in an ionic couple or with a covalent bond of the "σ" type;
- Z" represents an organic radical having from 5 to 30 carbon atoms, comprising a cyclopentadienyl anion bound to the metal $M^v$;
- "m" has the value 1 or 0 depending on whether Z" is present or absent in the compound having formula (X);
- "p" expresses the number of Z' groups necessary for neutralizing the formal oxidation charge "v" of the metal $M^v$ and has such values that p=(v−m−1).

The above formula (X) includes all compounds comprising a metal $M^v$ in an oxidation state greater than zero and at least one anion deriving from a ligand having the previous formula (II) according to what is specified above. These compounds can be of a saline ionic nature, especially with non-transition metals, or, when low energy orbitals of the metal are available to form bonds of the "π" type, these compounds are preferably in the form of coordinated complexes of a semi-covalent or covalent nature.

Of particular interest for their potential use as catalysts or components of catalysts for hydrogenation or polymerization processes of α-olefins, are compounds having formula (X) wherein $M^v$ is selected from metals of groups 3 to 10 of the periodic table, including metals of the group of lanthanides.

$M^v$ is preferably selected from metals of groups 4 to 6, and is more preferably Ti, Zr or Hf in oxidation state +4. In this case, particularly satisfactory results have been obtained when the Z" group in formula (X) is a second cyclopentadienyl anion, optionally, but not necessarily, selected from compounds having formula (II) above. In particular, a preferred object of the present invention relates to a bis-cyclopentadienyl complex of a transition metal $M^q$ of group 4 of the periodic table, having the following formula (XI):

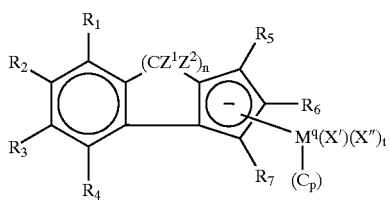

(XI)

wherein:
- each $R_1, R_2, R_3, R_4, R_5, R_6, R_7, Z^1$ and $Z^2$ group, and also "n", has the same meaning, both general and preferred, as the corresponding symbol in formulae (II) and (X) above;
- $M^q$ represents a metal selected from titanium, zirconium and hafnium having an oxidation state (or valence) "q" equal to 3 or 4, preferably 4;
- "t" has the value of 1 se the valence "q" of $M^q$ is 4, and the value of 0 if the valence of "q" of $M^q$ is 3;
- X' and X" each independently represent a group of a monovalent anionic nature σ-bound to the metal $M^q$, preferably selected from hydride, halide, a $C_1$–$C_{20}$ alkyl or alkylaryl group, a $C_3$–$C_{20}$ alkylsilyl group, a $C_5$–$C_{20}$ cycloalkyl group, a $C_6$–$C_{20}$ aryl or arylalkyl group, a $C_7$–$C_{20}$ alkoxyl or thioalkoxyl group, a $C_2$–$C_{20}$ carboxylate or carbamate group, a $C_2$–$C_{20}$ dialkylamide group and a $C_4$–$C_{20}$ alkylsilylamide group.
- $C_p$ represents any organic group containing a $\eta^5$-cyclopentadienyl or $\eta^5$-heterocyclopentadienyl ring, of an anionic nature, preferably having at least from 5 to 30 carbon atoms, coordinated to the metal $M^q$.

According to the present invention, in particular, the groups X' and X" having formula (XI) each independently represent a group of an anionic nature σ-bound to the metal $M^q$. Typical examples of X' and X" are hydride, halide, preferably chloride or bromide, a linear or branched alkyl group such as methyl, ethyl, butyl, isopropyl, isoamyl, octyl, decyl, benzyl, an alkylsilyl group such as, for example, trimethylsilyl, triethylsilyl or tributylsilyl, a cycloalkyl group such as cyclopentyl, cyclohexyl, 4-methylcyclohexyl, an aryl group such as phenyl or toluyl, an alkoxyl or thioalkoxyl group such as methoxyl, ethoxyl, iso- or sec-butoxyl, ethylsulfide, a carboxylate group such as acetate, trifluoroacetate, propionate, butyrate, pivalate, stearate, benzoate, or again a dialkylamide group such as diethylamide, dibutylamide, or alkylsilyl-amide, such as bis(trimetylsilyl)amide or ethyltrimetylsilylamide. The two X' and X" groups can also be chemically bound to each other and form a cycle having from 4 to 7 atoms different from hydrogen, also comprising the metal $M^q$. Typical examples of this aspect are divalent anionic groups such as the trimethylene or tetramethylene group, or the ethylenedioxy group. X' and X" groups which are particularly preferred for their accessibility and the easy preparation of the complexes which comprise them are chloride, $C_1$–$C_8$ alkoxide, methyl, ethyl, $C_3$–$C^{10}$ carboxylate.

Each $C_p$ group in formula (XI) contains a $\eta^5$-cyclopentadienyl ring coordinated to the metal $M^q$, which formally derives from a cyclopentadiene molecule, substituted or non-substituted, by extraction of an $H^+$ ion. The molecular bond of the π type and also the electronic and coordinative configuration of metallocene complexes of titanium, zirconium or hafnium, generally comprising two $\eta^5$-cyclopentadienyl groups, have been amply described in literature and are known to experts in the field.

The $C_p$ group having formula (XI) according to the present invention is selected, in particular, from known cyclopentadienyl, indenyl or fluorenyl groups, and their homologous products, in which one or more carbon atoms of the molecular skeleton (included or not included in the cyclopentadienyl ring), are substituted with a radical selected from the group consisting of halogen, preferably chlorine or bromine, a linear or branched alkyl group having from 1 to 10 carbon atoms, optionally halogenated, such as methyl, trifluoromethyl, ethyl, butyl, isopropyl, isoamyl, octyl, decyl, benzyl, an alkylsilyl group such as, for example, trimethylsilyl, triethylsilyl or tributylsilyl, a cycloalkyl group such as cyclopentyl, cyclohexyl, 4-methylcyclohexyl, an aryl group having from 6 to 10 carbon atoms, optionally halogenated, such as phenyl, pentafluorophenyl or toluyl, an alkoxyl or thioalkoxyl group such as methoxyl, ethoxyl, iso- or sec-butoxyl, ethylsulfide. Said Cp group may also comprise several condensed aromatic rings, as in the case, for example, of 4,5-benzoindenyl, and in a particularly preferred embodiment, is selected from anions of polycyclic cyclopentadienyl compounds having formula (II) described above.

For particular polymerization processes, especially when the steric control of the polymerization (iso- or syndiotactic orientation of α-olefins) is important, or the control of the insertion of co-monomers in the co-polymerization of ethylene, as is known to experts in the field, the above groups of an anionic nature, more specifically Z" in the complexes having formula (X) with $M^V$ a transition metal, and $C_p$ in complexes having formula (XI), can be covalently bound to the polycyclic cyclopentadienyl group deriving from compounds having formula (II), by means of a divalent hydrocarbon or silane group having from 1 to 15, preferably from 2 to 6, carbon atoms, to form a so-called "bridged" structure, according to the traditional terminology used in the field of metallocene compounds.

Non-limiting examples of compounds having general formula (X) and (XI) are those represented by the structures indicated hereunder, which, for the sake of simplicity, are not numbered:

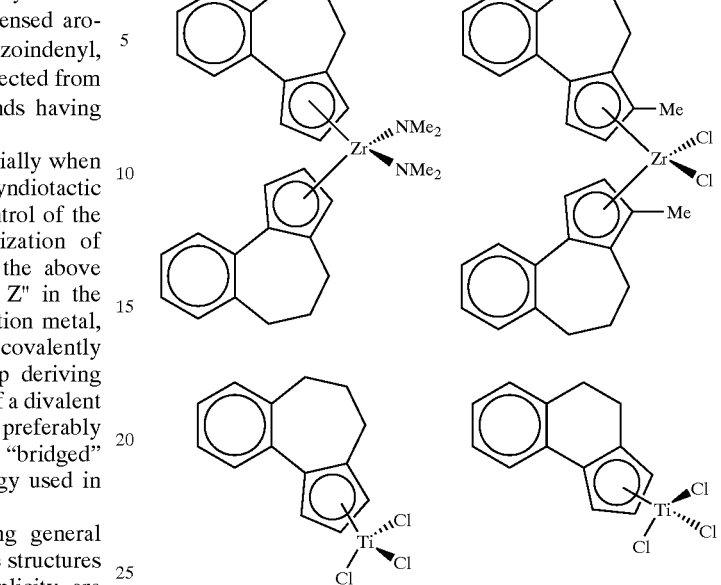

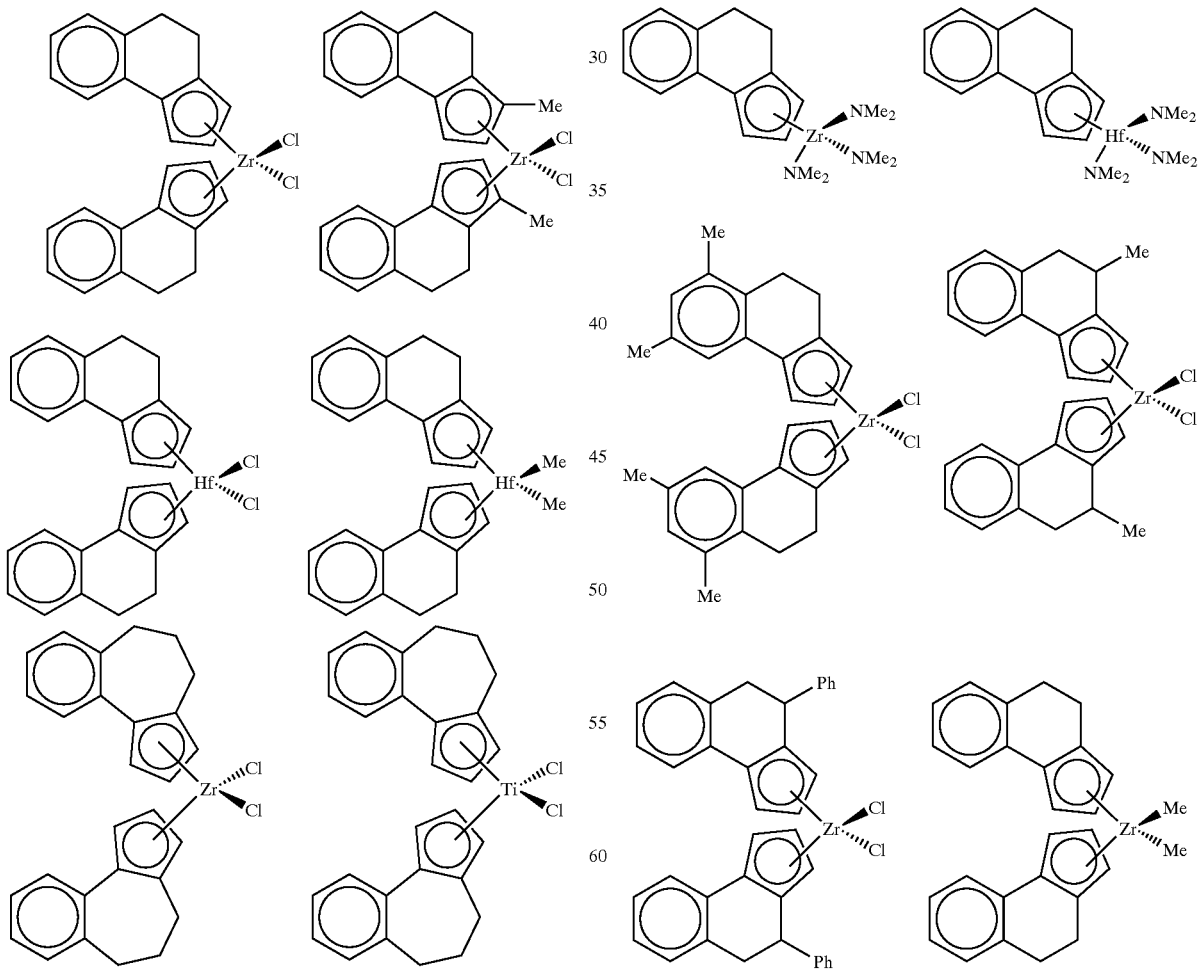

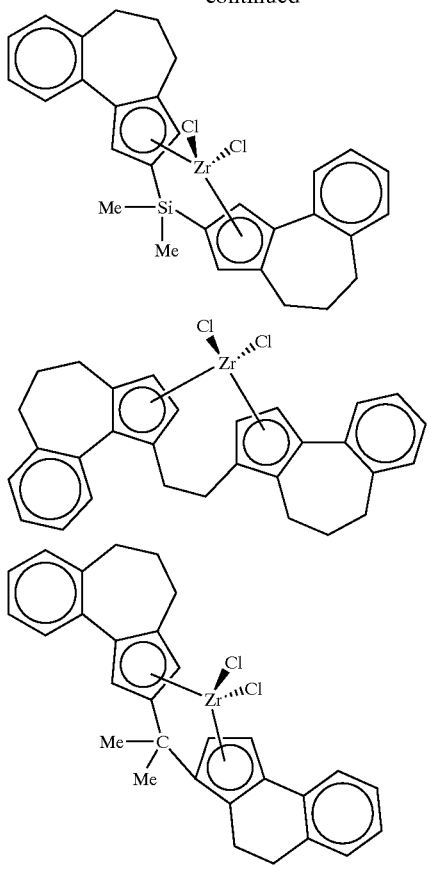

As mentioned above, the above complexes having formula (X) with certain transition metals, and more specifically complexes represented by formula (XI), can be advantageously used in the formation of catalysts for the polymerization and co-polymerization of olefins, combined with a suitable activator.

A further object of the present invention therefore relates to, and is claimed herein as such, a catalyst for the (co) polymerization of ethylene and other α-olefins, i.e. for the homo-polymerization of ethylene and other α-olefins, the co-polymerization of ethylene with one or more other co-polymerizable monomers, such as for example, α-olefins, conjugated or non-conjugated diolefins, styrene and its derivatives, etc., the co-polymerization of α-olefins with each other or with other monomers co-polymerizable therewith. This catalyst can be obtained from the combination (i.e. contact and reaction) of the above polycyclic metallocene complex having formula (X) or (XI) with an activator (or co-catalyst) selected from those known in the art of metallocene polymerization catalysis, particularly an organic compound of a metal M' selected from boron, aluminum, gallium and tin, or a combination of these compounds.

In particular, said catalyst in accordance with the present invention comprises the following two components in contact with each other, or the product of their reaction:
(i) at least one metallocene complex having the previous formula (X), wherein the metal $M^v$ is a metal of groups 4 to 6, preferably 4, of the periodic table;
(ii) a co-catalyst consisting of at least one organometallic compound of an element M' different from carbon and selected from elements of groups 2, 12, 13 or 14 of the periodic table as defined above.

According to the present invention, said element M' is preferably selected from boron, aluminum, zinc, magnesium, gallium and tin, more particularly boron and aluminum.

In a preferred embodiment of the present invention, the component (ii) is an organo-oxygenated derivative of aluminum, gallium or tin. This can be defined as an organic compound of M', in which the latter is bound to at least one oxygen atom and to at least one organic group consisting of an alkyl group having from 1 to 6 carbon atoms, preferably methyl.

According to this aspect of the invention, component (ii) is more preferably an aluminoxane. As is known, aluminoxanes are compounds containing Al—O—Al bonds, with a varying O/Al ratio, which can be obtained, under controlled conditions, by the reaction of an aluminum alkyl or aluminum alkyl halide, with water or other compounds containing pre-established quantities of water available, such as, for example, in the case of the reaction of aluminum trimethyl with aluminum sulfate hexahydrate, copper sulfate pentahydrate or iron sulfate pentahydrate. Aluminoxanes preferably used for the formation of the polymerization catalyst of the present invention are oligo- poly-meric, cyclic and/or linear compounds, characterized by the presence of repetitive units having the following formula (XII):

(XII)

wherein $R_8$ is a $C_1$–$C_6$ alkyl group, preferably methyl.

Each dialuminoxane molecule preferably contains from 4 to 70 repetitive units which may also not all be equal to each other, but contain different $R_8$ groups.

Said aluminoxanes, and particularly methylaluminoxane, are compounds which can be obtained by known methods in organometallic chemistry, for example, by the addition of aluminum trimethyl to a suspension in hexane of aluminum sulfate hydrate.

When used for the formation of a polymerization catalyst according to the present invention, the aluminoxanes (ii) are put in contact with said component (i) comprising the complex having formula (X) in such proportions that the atomic ratio between Al and the transition metal M is within the range of 10 to 10,000 and preferably from 100 to 5,000. The sequence with which the complex (i) and the aluminoxane (ii) are put in contact with each other, is not particularly critical.

In addition to the above aluminoxanes, the definition of component (ii) according to the present invention also comprises galloxanes (in which, in the previous formulae, gallium is present instead of aluminum) and stannoxanes, whose use as cocatalysts for the polymerization of olefins in the presence of metallocene complexes is known, for example, from patents U.S. Pat. Nos. 5,128,295 and 5,258,475.

According to another preferred aspect of the present invention, said catalyst can be obtained by putting component (i) consisting of at least on complex having formula (X), in contact with component (ii) consisting of at least one compound or a mixture of organometallic compounds of M' capable of reacting with the complex having formula (X), extracting from this a σ-bound group Z' or Z" to form, on the one hand at least one neutral compound, and on the other hand an ionic compound consisting of a metallocene cation containing the metal $M^v$ and an organic non-coordinating anion containing the metal M', whose negative charge is delocalized on a multicentric structure.

Components (ii) suitable as ionizing systems of the above type are preferably selected from the voluminous organic compounds of boron and aluminum, such as for example, those represented by the following general formulae:

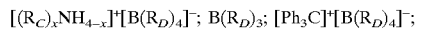

wherein the deponent "x" is an integer ranging from 0 to 3, each $R_C$ group independently represents an alkyl or aryl radical having from 1 to 10 carbon atoms and each $R_D$ group independently represents an aryl radical partially or, preferably, totally fluorinated, having from 6 to 20 carbon atoms.

Said compounds are generally used in such quantities that the ratio between the atom M' of component (ii) and the atom $M^v$ in the metallocene complex is within the range of 0.1 to 15, preferably from 0.5 to 10, more preferably from 1 to 6.

Component (ii) can consist of a single compound, normally an ionic compound, or a combination of this compound with MAO, or, preferably, with an aluminum trialkyl having from 1 to 8 carbon atoms in each alkyl residue, such as for example $AlMe_3$, $AlEt_3$, $Al(i-Bu)_3$.

In general, the formation of the ionic metallocene catalyst, in accordance with the present invention, is preferably carried out in an inert liquid medium, more preferably hydrocarbon. The selection of components (i) and (ii), which are preferably combined with each other, as well as the particular method used, can vary depending on the molecular structures and result desired, according to what is described in detail in specific literature available to experts in the field.

Examples of these methods are qualitatively schematized in the list provided hereunder, which however does not limit the overall scope of the present invention:

($m_1$) by contact of a metallocene having general formula (X), or preferably (XI), wherein at least one, preferably all, of the substituents Z' and Z" is hydrogen or an alkyl radical, with an ionic compound whose cation is capable of reacting with one of the substituents to form a neutral compound, and whose anion is voluminous, non-coordinating and capable of delocalizing the negative charge;

($m_2$) by the reaction of a metallocene having the previous formula (X), or preferably (XI), with an alkylating agent, preferably an aluminum trialkyl, used in molar excess of 10/1 to 500/1, followed by the reaction with a strong Lewis acid, such as for example, tris(pentafluorophenyl) boron a in more or less stoichiometric quantity or in slight excess with respect to the metal $M^v$;

($m_3$) by contact and reaction of a metallocene having the previous formula (X), or preferably (XI), with a molar excess of 10/1 to 1000/1, preferably from 100/1 to 500/1 of an aluminum trialkyl or an alkylaluminum halide represented by the following formula $$AlR^9{}_m X_{3-m},$$

wherein: $R^9$ is a linear or branched $C_3$–$C_{20}$ alkyl group, or one of their mixtures, X is a halogen, preferably chlorine or bromine, and "m" is a decimal number ranging from 1 to 3 extremes included;

followed by the addition to the composition thus obtained, of at least an ionic compound of the type described above in such quantities that the ratio between B or Al and the atom $M^v$ in the metallocene complex is within the range of 0.1 to 15, preferably from 1 to 6.

Examples of ionizing ionic compounds or multicomponent reactive systems capable of producing an ionic catalytic system by reaction with a metallocene complex, according to the present invention, are described in the following patent publications, whose content in herein incorporated as reference:

European patent application, published under the Nr.: EP-A 277,003, EP-A 277,004, EP-A 522,581, EP-A 495,375, EP-A 520,732, EP-A 478,913, EP-A 468,651, EP-A 427,697, EP-A 421,659, EP-A 418,044;

International patent applications published under the Nr.: WO 92/00333, WO 92/05208; WO 91/09882;

Patents U.S. Pat. Nos. 5,064,802, 2,827,446, 5,066,739.

Non-limiting examples of complex-cocatalyst combinations suitable for the preparation of ionic catalytic systems in accordance with the present invention are schematized hereunder in table (I), with reference to the respective precursors from whose combination they can be obtained. Any compound of any column can be combined, if necessary, with any compound of the remaining ones, according to the method indicated.

TABLE (I)

| preparation of ionic catalysts according to the present invention | | |
|---|---|---|
| Method | Metallocene with formula (XI) | Cocatalyst (ii) |
| ($m_1$) | $(THAZ)_2ZrMe_2$ | |
| | $(THAZ)_2TiMe_2$ | |
| | $(DHBI)_2ZrMe_2$ | $[Ph_3C]^+[B(C_6F_5)_4]^-$ |
| | $(DHBI)_2HfH_2$ | |
| | $(DHBI) CpZrMe_2$ | $[Bu_3NH]^+[B(C_6F_5)_4]^-$ |
| | $(THAZ)_2TiPr^i{}_2$ | |
| | $(DHBI)_2ZrH_2$ | $[PhNMe_2H]^+[B(C_6F_5)_4]^-$ |
| | $(DHBI)_2TiBz_2$ | |
| ($m_3$) | $(7,9-Me_2-DHBI)_2ZrCl_2$ | |
| | $(DHBI)_2TiBr_2$ | |
| | $(THAZ)_2ZrCl_2$ | $[Ph_3C]^+[B(C_6F_5)_4]^-$ |
| | $(DHBI)_2Zr(NMe_2)_2$ | |
| | $(DHBI)_2ZrCl_2$ | $AlEt_3$ |
| | $(DHBI)_2HfCl_2$ | $[PhNMe_2H]^+[B(C_6F_5)_4]^-$ |
| | $(DHBI)_2TiCl_2$ | $AlBu^i{}_3$ |
| | $(DHBI) (Ind) ZrCl_2$ | $[Bu_3NH]^+[B(C_6F_5)_4]^-$ |
| | $(THAZ)_2HfCl_2$ | |
| | $(THAZ)_2Ti(NMe_2)_2$ | |

Abbreviations: Me = methyl, Et = ethyl, Bu = n-butyl, $Bu^i$ = iso-butyl, Ph = phenyl, Bz = benzyl, $Pr^i$ = isopropyl, Cp = cyclopentadienyl Ind = indenyl, DHBI = 4,5-dihydro-benzo[d]indenyl 7,9-$Me_2$-DHBI = 7,9-dimethyl-4,5-dihydro-benzo[d]indenyl, THAZ = 4,5,6-trihydro benzo[e] azulenyl.

Also included in the scope of the present invention are those catalysts comprising two or more complexes having formula (X) or (XI) mixed with each other. Catalysts of the present invention based on mixtures of complexes having different catalytic activities can be advantageously used in polymerization when a wider molecular weight distribution of the polyolefins thus produced is desired.

In a particularly preferred embodiment of the present invention, the metallocene component (i) of said catalyst consists of a complex selected from those represented by the previous formula (XI), especially with the metal $M^q$ in oxidation state +4, or a mixture of these complexes.

According to another aspect of the present invention, in order to produce solid components for the formation of catalysts for the polymerization of olefins, the above complexes can also be supported on inert solids, preferably consisting of oxides of Si and/or Al, such as, for example, silica, alumina or silica-aluminates. For supporting of said catalysts, the known supporting techniques can be used, normally comprising contact, in a suitable inert liquid medium, between the carrier, optionally activated by heating to temperatures exceeding 200° C., and one or both of components (i) and (ii) of the catalyst of the present invention. For the purposes of the present invention, it is not necessary for both components to be supported, as it is also possible for only the complex having formula (X), or preferably (XI), or the organic compound of B, Al, Ga or Sri as defined above, to be present on the surface of the carrier. In the latter case, the component which is not present on the surface is subsequently put in contact with the supported component, at the moment of the formation of the catalyst active for the polymerization.

Also included in the scope of the present invention are the complexes, and catalytic systems based on these, which have been supported on a solid by means of the functionalization of the latter and formation of a covalent bond between the solid and a metallocene complex included in formula (X), or preferably (XI), above.

A particular method for the formation of a supported catalyst according to the present invention comprises prepolymerizing a relatively small fraction of monomer or mixture of monomers in the presence of the catalyst, so as to include this in a solid micro-particulate, which is then fed to the actual reactor itself for completing the process in the presence of an additional α-olefin. This provides a better control of the morphology and dimensions of the polymeric particulate obtained at the end.

One or more other additives or components can be optionally added to the catalyst according to the present invention, as well as the two components (i) or (ii), to obtain a catalytic system suitable for satisfying specific requests. The catalytic systems thus obtained should be considered as being included in the scope of the present invention. Additives or components which can be included in the preparation and/or formulation of the catalyst of the present invention are inert solvents such as, for example, aliphatic and/or aromatic hydrocarbons, aliphatic and aromatic ethers, weakly coordinating additives (Lewis bases) selected, for example, from non-polymerizable olefins, ethers, tertiary amines and alcohols, halogenating agents such as silicon halides, halogenated hydrocarbons, preferably chlorinated, and the like, and again all other possible components normally used in the art for the preparation of the traditional homogeneous catalysts of the metallocene type for the (co)polymerization of ethylene and α-olefins.

Components (i) and (ii) form the catalyst of the present invention by contact with each other, preferably at temperatures ranging from room temperature to 60° C. and for times varying from 10 seconds to 1 hour, more preferably from 30 seconds to 10 minutes.

The catalysts according to the present invention can be used with excellent results in substantially all known (co) polymerization processes of α-olefins, either in continuous or batchwise, in one or more steps, such as, for example, processes at low (0.1–1.0 MPa), medium (1.0–10 MPa) or high (10–150 MPa) pressure, at temperatures ranging from 20° to 240° C., optionally in the presence of an inert diluent. Hydrogen can be conveniently used as molecular weight regulator.

A further object of the present invention therefore relates to a process for the (co)polymerization of α-olefins, comprising polymerizing said α-olefin, or copolymerizing one or more of said α-olefins, under suitable pressure and temperature conditions, in the presence of at least one of the catalysts according to the present invention, as described above.

These processes can be carried out in solution or suspension in a liquid diluent normally consisting of an aliphatic or cycloaliphatic saturated hydrocarbon, having from 3 to 8 carbon atoms, but which can also consist of a monomer as, for example, in the known co-polymerization process of ethylene and propylene in liquid propylene. The quantity of catalyst introduced into the polymerization mixture is preferably selected so that the concentration of the transition metal $M^v$ or $M^q$ ranges from $10^{-5}$ to $10^{-8}$ moles/liter.

Alternatively, the polymerization can be carried out in gas phase, for example, in a fluid bed reactor, normally at pressures ranging from 0.5 to 5 MPa and at temperatures ranging from 50 to 150° C.

α-olefins which can be polymerized or copolymerized according to the process of the present invention are generally all olefinically unsaturated hydrocarbons having at least one $>C=CH_2$ double bond in so-called -α, or primary, position. Said α-olefins comprise ethylene and its higher homologous products, preferably having from 3 to 15 carbon atoms, such as, for example, propylene, 1-butene, butadiene, 1-hexene, 1-octene, 1,4-hexadiene and styrene. Particular non-primary olefins, having the double bond included in a stretched ring, such as for example, dicyclopentadiene, can be equally (co)polymerized in the presence of the catalyst of the present invention.

According to a particular aspect of the present invention, the catalyst for the (co)polymerization of α-olefins is prepared separately (preformed) by contact of components (i) and (ii), and is subsequently introduced into the polymerization environment. The catalyst can be charged first into the polymerization reactor, followed by the reagent mixture containing the olefin or mixture of olefins to be polymerized, or the catalyst can be charged into the reactor already containing the reagent mixture, or finally, the reagent mixture and the catalyst can be contemporaneously fed into the reactor.

According to another aspect of the present invention, the catalyst is formed "in situ", for example by introducing components (i) and (ii) separately into the polymerization reactor containing the selected olefinic monomers.

The catalysts according to the present invention can be used with excellent results in the polymerization of ethylene to give linear polyethylene and in the copolymerization of ethylene with propylene or higher α-olefins, preferably having from 4 to 10 carbon atoms, to give copolymers having different characteristics depending on the specific polymerization conditions and on the quantity and structure of the α-olefin. For example, linear polyethylenes can be obtained, with a density ranging from 0.880 to 0.940, and with molecular weights ranging from 10,000 to 2,000,000. The α-olefins preferably used as comonomers of ethylene in the production of low or medium density linear polyethylene (known with the abbreviations ULDPE, VLDPE and LLDPE depending on the density), are 1-butene, 1-hexene and 1-octene.

The catalyst of the present invention can also be conveniently used in copolymerization processes of ethylene and propylene to give saturated elastomeric copolymers vulcanizable by means of peroxides and extremely resistant to aging and degradation, or in the terpolymerization of ethylene, propylene and a non-conjugated diene, having from 5 to 20 carbon atoms, to obtain vulcanizable rubbers of the EPDM type. In the case of these latter processes, it has been found that the catalysts of the present invention allow the production of polymers having a particularly high diene content and average molecular weight, under the polymerization conditions.

In the case of the preparation of EPDM, the dienes which can be used for the preparation of said terpolymers are preferably selected from:

linear chain dienes such as 1,4-hexadiene and 1,6-octadiene;

branched dienes such as 5-methyl-1,4-hexadiene; 3,7-dimethyl-1,6-octadiene; 3,7-dimethyl-1,7-octadiene;

dienes with a single ring such as 1,4-cyclohexadiene; 1,5-cyclo-octadiene; 1,5-cyclododecadiene;

dienes having bridged condensed rings such as dicyclopentadiene; bicyclo[2.2.1]hepta-2,5-diene; alkenyl, alkylidene, cycloalkenyl and cycloalkylidene norbornenes such as 5-methylene-2-norbornene, 5-ethylidene-2-borbornene (ENB), 5-propenyl-2-norbornene.

Among the non-conjugated dienes typically used for preparing these copolymers, dienes containing at least one double bond in a stretched ring are preferred, even more preferably 5-ethylidene-2-norbornene (ENB), and also 1,4-hexadiene and 1,6-octadiene.

In the case of EPDM terpolymers, it is convenient for the quantity of dienic monomer not to exceed 15% by weight, and it is preferably from 2 to 10% by weight. The propylene content on the other hand ranges from 20 to 50° by weight.

The catalysts of the present invention can also be used in homo- and co-polymerization processes of α-olefins according to the known techniques, giving, with excellent yields, atactic, isotactic or syndiotactic polymers, depending on the structure and geometry of the metallocene complex having formula (XI). α-olefins suitable for the purpose are those having from 3 to 20 carbon atoms, optionally also comprising halogens or aromatic nuclei such as, for example, propylene, 1-butene, 1-hexene, 4-methyl-1-pentene, 1-decene and styrene.

The present invention is further described by the following examples, which, however, are provided for purely illustrative purposes and do not limit the overall scope of the invention itself.

EXAMPLES

The analytical techniques and characterization methods used in the examples are listed below and are briefly de-scribed.

The characterization by means of $^1$H-NMR and $^{13}$C-NMR spectroscopy mentioned in the following examples was carried out on a nuclear magnetic resonance spectrometer mod. Bruker MSL-300.

The characterization of the products and organic intermediates by means of gaschromatography/mass spectrography (GC-mass) was carried out with a Finnigan TSQ 700 instrument.

The measurement of the molecular weights of the olefinic polymers was carried out by means of Gel-Permeation Chromatography (GPC). The analyses of the samples were effected in 1,2,4-trichlorobenzene (stabilized with Santonox) at 135° C. with a WATERS 150-CV chromatograph using a Waters differential refractometer as detector.

The chromatographic separation was obtained with a set of μ-Styragel HT columns (Waters) of which three with pore dimensions of $10^3$, $10^4$, $10^5$ Å respectively, and two with pore dimensions of $10^6$ Å, establishing a flow-rate of the eluant of 1 ml/min.

The data were obtained and processed by means of Maxima 820 software version 3.30 (Millipore); the number ($M_n$) and weight ($M_w$) average molecular weight calculation was carried out by universal calibration, selecting polystyrene standards with molecular weights within the range of 6,500,000–2,000, for the calibration.

The determination of the content of units deriving from propylene and possible diene in the polymers is carried out (according to the method of the Applicant) by means of IR on the same polymers in the form of films having a thickness of 0.2 mm, using an FTIR Perkin-Elmer spectrophotometer model 1760. The intensity of the characteristic peaks is measured, of propylene at 4390 cm$^{-1}$ and ENB at 1688 cm$^{-1}$ respectively, in relation to the peak at 4255 cm$^{-1}$, and the quantity is determined using a standard calibration curve.

The Melt Flow Index (MFI) of the polymers is determined in accordance with the regulation ASTM D-1238 D.

In the preparation of the examples, the commercial reagents listed below, were used:

| | |
|---|---|
| α-tetralone | ALDRICH |
| α-benzosuberone | ALDRICH |
| 5,7-dimethyl-1-tetralone | ALDRICH |
| diethylcarbonate | CARLO ERBA |
| propargylchloride | FLUKA |
| methyllithium (LiMe) 1.6 M in diethyl ether | ALDRICH |
| butyllithium (LiBu) 2.5 M in hexane | ALDRICH |
| zirconium tetrachloride (ZrCl$_4$) | FLUKA |
| methylalumoxane (MAO) (Eurecene 5100 10T, 10% weight/volume of Al in toluene) | WITCO |

The reagents and/or solvents used and not indicated above are those commonly used both in bench and on industrial scale and can be easily found at all commercial operators specialized in the field.

Example 1

Synthesis of bis-(4,5-dihydro-benzo[d]indenyl)-zirconium dichloride (XVIII)

1a) Synthesis of 1-oxo-2-ethyloxycarbonyl-1,2,3,4-tetrahydronaphthalene (XIII)

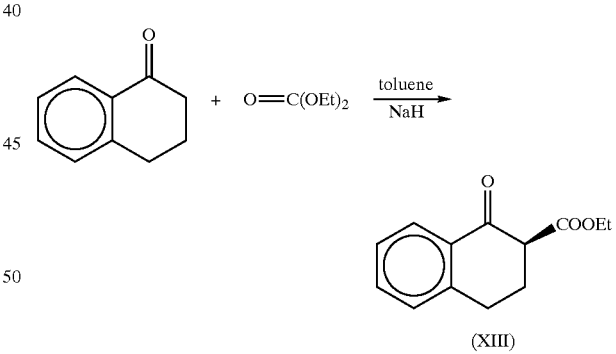

(XIII)

2.5 liters of commercial toluene and 22 g of NaH (0.96 moles) are charged into a 3 liter three-necked glass flask, equipped with a mechanical stirrer and cooler, the suspension is left under stirring at room temperature for 2 hours and 115 ml of diethylcarbonate (0.94 moles) are then added. The mixture is then heated to 80–90° C. and 38 ml of α-tetralone (0.28 moles) diluted in 80 ml of toluene are added, in about 3 hours, by means of a drip funnel. The reaction mixture is maintained at 90° C. and the trend is periodically controlled by means of thin layer chromatography (T.L.C.) on samples removed for the purpose. After about 24 hours, the complete disappearance of α-tetralone is observed.

The reaction mixture is carefully poured into about 1 kg of ice containing 50 ml of glacial acetic acid. The phases are separated and the aqueous phase is repeatedly extracted with ethyl ether, the organic extracts are subsequently washed with water saturated with NaHCO₃ and then with water until neutrality. The organic phase, after anhydrification on Na₂SO₄ is evaporated at reduced pressure until 53 g of a red-colored oily residue is obtained, which is purified by distillation on a 20 cm. vigreux column. 42.65 g (density= 1.15 g/cm³) of the desired 1-oxo-2-ethyloxycarbonyl-1,2,3,4-tetrahydronaphthalene having formula (XIII) in the above scheme, are obtained. The NMR spectrum shows that the product is present in solution in ketonic and enolic forms in a ratio of 55/45 respectively.

¹H NMR (CDCl₃ δ, ppm rel. to TMS): 12.48 (s, 0.45H enol); 7.81–7.14 (m, 4H); 4.24 (dq, 2H); 3.59 (dd, 0.55H ketone); 3.1–2.2 (m, 4H); 1.31 (dt, 3H).

1b) Synthesis of 1-oxo-2-prop-2-inyl-2-ethoxycarbonyl-1,2,3,4-tetrahydro-naphthalene (XIV)

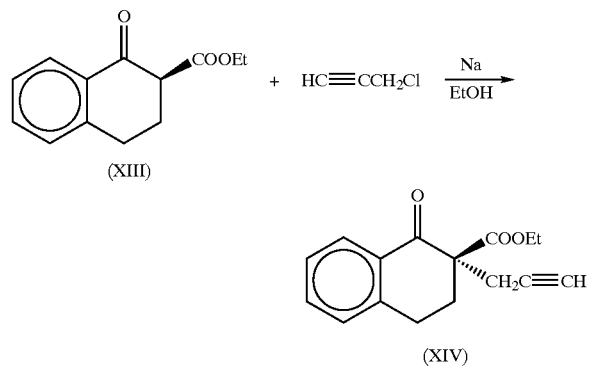

4.1 g (0.178 moles) of metal sodium are charged into a 1 liter flask and 500 ml of anhydrous ethanol are added. After complete dissolution of the metal sodium, 42 g (0.175 moles) of 1-oxo-2-ethoxycarbonyl-1,2,3,4-tetrahydronaphthalene (XIII) obtained as described above, are added. A light yellow milky solid is immediately formed. The mixture is heated to the reflux temperature of the solvent, and 42 ml (0.4 moles) of propargyl chloride diluted with 30% of toluene are then added by means of a drip funnel in about 2 hours. At the end of the addition, the mixture is kept at reflux temperature for about 3 hours and is then cooled to room temperature and left under stirring for the whole night. In this phase there is the progressive disappearance of the yellow milky solid with the formation of a colorless crystalline solid. About 400 ml of EtOH are removed by evaporation at reduced pressure, the mixture is subsequently hydrolyzed with water and ice and extracted with various portions of ethyl ether. The ether extracts are joined, washed with water until neutrality and dried on anhydrous Na₂SO₄. The solvent is then evaporated at reduced pressure and 45 g of an oily reddish-brown residue is obtained, consisting of 70% by weight of the desired product (XIV) (GC analysis, 70% yield).

¹H NMR (CDCl₃ δ, ppm rel. to TMS): 7.4–7.1 (m, 4H); 4.14 (q, 2H); 3.2–2.95 (m, 2H); 2.88 (d, 2H); 2.7–2.3 (m, 2H); 2.00 (t, 1H); 1.53 (t, 3H).

1c) Synthesis of 1-oxo-2-(2-oxo-propyl)-2-ethoxycarbonyl-1,2,3,4-tetrahydro-naphthalene (XV):

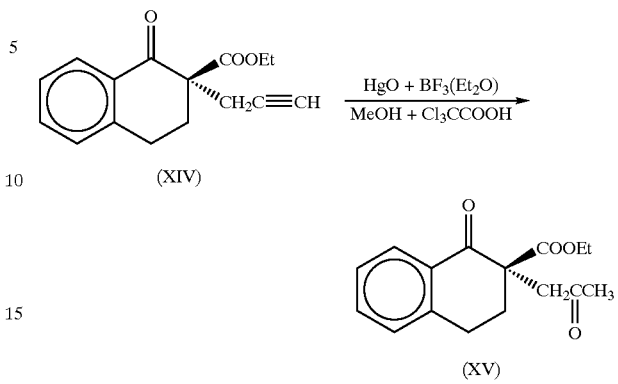

The following products are charged in order into a 500 ml glass flask: 200 ml of methanol, 0.32 g (1.5 mmoles) of mercury oxide, 1.4 ml (11 mmoles) of borontrifluoride etherate and 0.07 g (0.4 mmoles) of trichloroacetic acid.

45 g (0.123 moles) of the compound having formula (XIV) obtained as described in the previous step (b), dissolved in 50 ml of methanol, are added to the suspension thus obtained. The reaction mixture is then left under stirring at room temperature for 18 hours and is subsequently hydrolyzed with water and extracted with various portions of ethyl ether. The ether extracts are joined, anhydrified on Na₂SO₄ and concentrated by evaporation at reduced pressure, obtaining at the end an oily red residue containing 43.5 g of the desired product having formula (XV) (65% purity upon GC analysis, 86% yield). Analyses show that both ethyl ester (45%) and methyl ester (55%) deriving from the transesterification of the product (XV) due to the use of methanol as solvent, are present. The product is not additionally purified.

¹H NMR (CDCl₃ δ, ppm rel. to TMS): 7.4–7.1 (m, 4H); 4.14 (q, 0.45×2H, ethyl ester); 3.67 (s, 0.55×3H, methyl ester); 3.2–2.3 (m, 6H); 2.22 (s, 3H); 1.29 (t, 0.45×3H, ethyl ester).

1d) Synthesis of 3,3a,4,5-tetrahydro-cyclopenta[a]naphthalen-2-one (XVI)

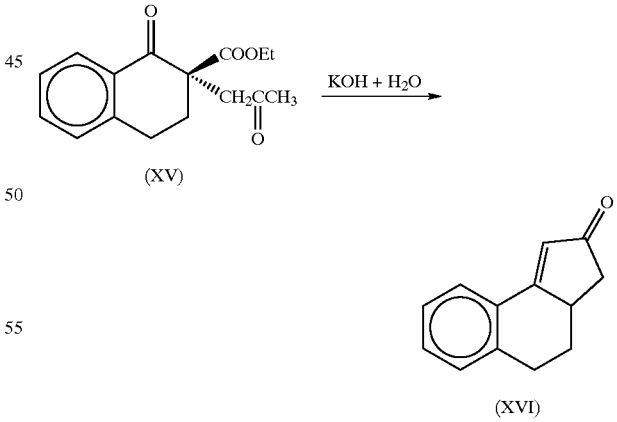

500 ml of water and 40 g of KOH are charged into a 1 liter glass flask, containing 43 g of 2-ethoxycarbonyl-2-(2-oxopropyl)-α-tetralone (XV), 65% purity, obtained as described above. The mixture is then heated to reflux temperature for 10 hours, the reaction trend being followed by means of TLC.

The aqueous suspension is cooled to room temperature and extracted with various portions of ethyl ether, the organic fractions are joined and subsequently washed with water saturated with NH₄Cl, then with water until neutrality and dried on anhydrous Na₂SO₄. The solvent is removed under vacuum and 26.5 g of an oily red residue are obtained, which contains 65% (GC analysis) of the product (XVII) (yield 93%), which is purified by means of flash chromatography, using a 70/30 (by volume) mixture of hexane/ethyl acetate as eluant and SiO₂ (Merck) 32–60 Å as stationary phase. At the end of this operation, 9.4 g (51 mmoles) of the desired pure product having formula (XVII) are recovered.

¹H NMR (CDCl₃ δ, ppm rel. to TMS): 7.65 (d, 1H); 7.4–7.2 (m, 3H); 6.38 (d, 1H,); 3.1–2.9 (m, 3H); 2.84–2.72 (dd, 1H); 2.35–2.26 (m, 1H); 2.25–2.14 (dd, 1H); 1.77–1.55 (m, 1H).

1e) Synthesis of 3a,4,5-trihydro-cyclopenta[a]naphthalene (XVII)

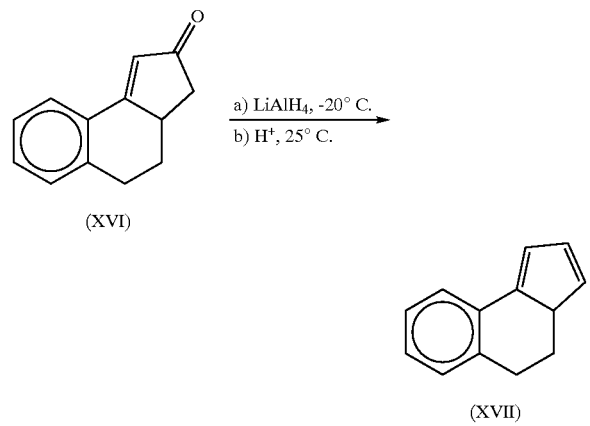

3.5 g (92 mmoles) of LiAlH₄ and 250 ml of ethyl ether are charged into a 500 ml flask. 50 ml of a solution of ethyl ether containing 4.0 g (21,5 mmoles) of the product having formula (XVI) are added at −20° C. by means of a drip funnel over a period of about 1 hour, to the suspension thus formed. At the end of the addition, the temperature is brought to 25° C. and the mixture is left under stirring for 2 hours, obtaining a yellow mixture. This reaction mixture is carefully poured into water and ice and is then acidified with HCl, extracted with various portions of ethyl ether, the organic phase is dried on anhydrous Na₂SO₄, and finally the solvent is evaporated at reduced pressure, obtaining 2.9 g of the desired pure product (XVII), as a light yellow granular solid (yield 80%).

1f) Synthesis of bis-(4,5-dihydro cyclopenta[a]naphthalenyl zirconium dichloride (XVIII)

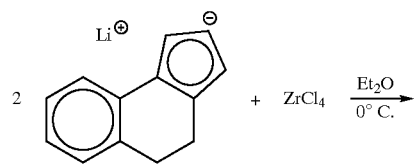

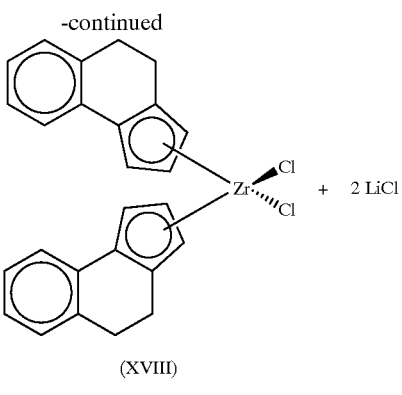

2.9 g (17.3 mmoles) of the cyclopentadienyl compound having formula (XVII) obtained according to the previous step (e) and 200 ml of hexane are charged into a 500 ml flask. 16 ml (25.6 mmoles) of LiBu (1.6 M in hexane) are then added in about 30 minutes by means of a drip funnel. A yellow solid is rapidly formed. The mixture is left under stirring at room temperature for 18 hours, the solid is then recovered by filtration, washing with three 20 ml portions of hexane and the product is dried at reduced pressure, thus obtaining 0.7 g of the lithium salt of the cyclopentadienyl compound having formula (XVII) (24% yield).

The lithium salt thus obtained and 100 ml of ethyl ether are charged into a 250 ml flask. A suspension is obtained which is cooled to 0° C. and 0.5 g (2.14 mmoles) of ZrCl₄ are added. The reaction mixture is then left under stirring for 4 hours in this phase; a yellowish colouring is obtained and a white solid is formed which can be easily decanted. The suspension is then filtered and the solid washed with three 10 ml portions of ethyl ether. The ether solution is evaporated under vacuum, at room temperature, and in this way a solid yellow residue remains, from which the complex (XVIII), pure by crystallization from toluene pentane, is obtained.

¹H NMR (CD₂Cl₂ δ, ppm rel. to TMS): 7.41 (d, 1H); 7.35–7.15 (m, 7H); 6.36 (t, 1H); 6.30 (dt, 2H); 6.05 (dd, 1H); 5.90 (dd, 1H); 5.77 (t, 1H); 3.10–2.95 (m, 3H); 2.90–2.60 (m, 9H).

Example 2

Synthesis of bis-(4,5,6-trihydro-benzo[e]azulenyl) zirconium dichloride (XXIV).

2a) Synthesis of 5-oxo-6-ethoxycarbonyl-6,7,8,9-tetrahydro-5H-benzocycloheptadiene (XIX)

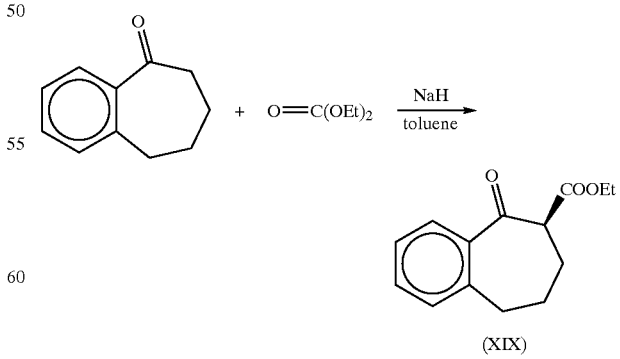

11.5 g of NaH (0.48 moles) in 600 ml of commercial toluene are suspended in a 1 liter glass flask, equipped with a bubble cooler, and the whole mixture is maintained under stirring at room temperature for 2 hours. 63 ml of diethyl carbonate (0.52 moles) are then added and the mixture is heated to 90° C., after which 25 g of α-benzosuberone (0.156 moles) dissolved in 50 ml of toluene are added, by means of a drip funnel in about 3 hours. The reaction trend is controlled by means of T.L.C. and after about 4 hours at 90° C., the complete disappearance of α-benzosuberone is observed. The reaction mixture is carefully poured into about 1 kg of ice containing 50 ml of glacial acetic acid. The phases are separated and the aqueous phase is repeatedly extracted with ethyl ether, the organic extracts are subsequently joined and washed with water saturated with $NaHCO_3$ and then with water until neutrality. The organic phase is anhydrified on $Na_2SO_4$ and the solvents are completely removed at reduced pressure. 33.2 g of a yellow oil consisting of the desired ketoester having formula (XIX) in the above scheme, are obtained, with a 90% purity. The $^1H$ NMR spectrum shows that the product (XIX) is present in solution in ketonic and enolic forms in a ratio of 25 to 75% respectively.

$^1H$ NMR (CDCl$_3$ δ, ppm rel. to TMS): 12.70 (s, 0.75H enol); 7.7–7.1 (m, 4H); 4.28 (dq, 2H); 3.78 (dd, 0.25H ketone); 2.93 (m, 2×0.25H ketone); 2.63 (t, 2×0.75H enol); 2.3×1.8 (m, 4H); 1.34 (t, 3×0.75H enol); 1.25 (t, 3×0.25H ketone).

2b) Synthesis of 5-oxo-6-ethoxycarbonyl-6-prop-2-inyl-6,7,8,9-tetrahydro-5H-benzocycloheptadiene (XX).

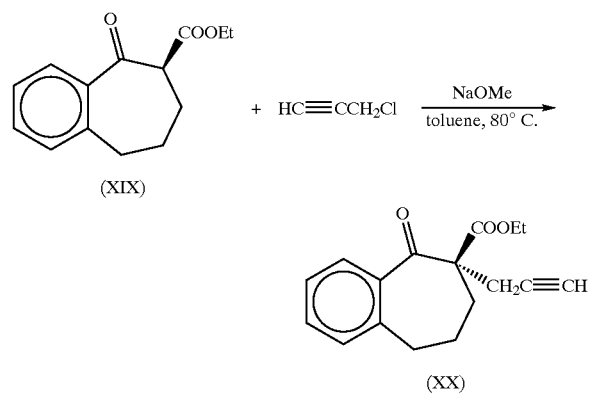

4.5 g of metal sodium and 100 ml of anhydrous methanol are charged into a 500 ml glass flask. The mixture is left under stirring until complete dissolution of the sodium, after which the solvent is evaporated and the solid obtained is further dried in order to remove most of the methanol present.

The colourless solid thus obtained is dispersed in 200 ml of toluene, the ketoester (XIX) is added, the suspension is then heated to 80° C. and 31 ml (0.295 moles) of propargyl chloride in a solution at 70% in toluene are added, by means of a drip funnel, in about an hour. After 24 hours, G.C. analysis of the reaction mixture shows that all the ketoester (XIX) has been converted. The reaction mixture is then hydrolyzed with water and ice and extracted with various portions of ethyl ether. The ether extracts are joined and subsequently washed with water and dried on anhydrous $Na_2SO_4$. The solvent is then removed at reduced pressure and 38.5 g of a reddish-brown oil are thus obtained, in which about 35% of the desired product having formula (XX) is present, as determined on the basis of GC-mass analysis.

2c) Synthesis of 5-oxo-6-ethoxycarbonyl-6-(2-oxo-propyl)-6,7,8,9-tetrahydro-5H-benzocycloheptadiene (XXI):

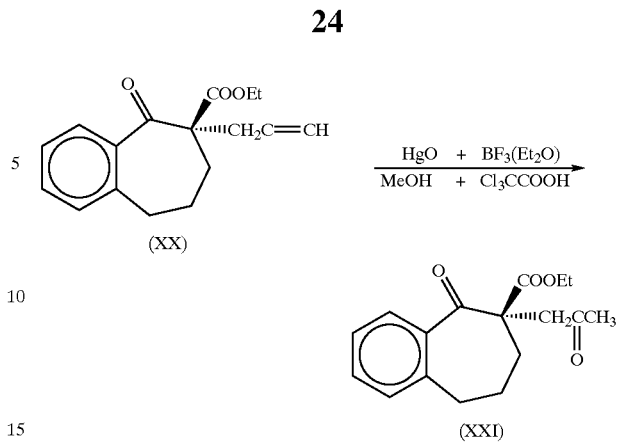

The following products are charged in order into a 500 ml flask, at room temperature: 250 ml of methanol, 1.2 g (5.6 mmoles) of mercury oxide HgO, 1.5 ml (11.8 mmoles) of boron trifluoride etherate, 0.07 g (0.4 mmoles) of trichloroacetic acid and 38.5 g of the impure product (35%) having formula (XX) obtained as described above. The dark suspension thus formed is reacted by heating to 50° C. for 4 hours. At the end, the methanol is removed at reduced pressure and water is added to the residue, forming a suspension which is extracted with various portions of ethyl ether. These are joined, washed with water until neutrality and anhydrified on $Na_2SO_4$. The ether solution is dried obtaining 38 g of a reddish-brown oil containing about 35% of the desired product (XXI).

2d) Synthesis of 3,4,5,6-tetrahydro-3H-benzo[e]azulen-2-one (XXII):

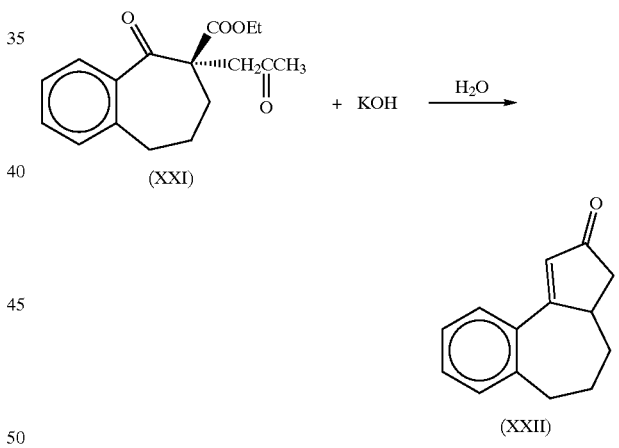

55 g (0.98 moles) of potassium hydroxide are dissolved in 300 ml of water in a 500 ml flask and 38 g of compound (XXI), obtained as described above, are added. A suspension is formed, which is heated to reflux temperature for 12 hours, the reaction being followed by G.C.

At the end of the reaction, the suspension is cooled to room temperature and extracted with various portions of ethyl ether. The ether extracts are subsequently washed with water saturated with $NH_4Cl$ and subsequently with water until neutrality, then dried on anhydrous $Na_2SO_4$. After evaporation of the solvent at reduced pressure, 13 g of an oily red liquid are obtained, which is purified by means of flash chromatography on a column, using a 70/30 (by volume) mixture of hexane/ethyl acetate as eluant and $SiO_2$ (Merck) 32–60 as stationary phase. 2.2 g of the desired pure product (XXII) are obtained at the end.

$^1$H NMR (CDCl$_3$ δ, ppm rel. to TMS): 7.4–7.1 (m, 4H); 6.20 (d, 1H); 3.2–2.6 (m, 4H); 2.4–1.2 (m, 5H).

2e) Synthesis of 3a,4,5,6-tetrahydro-benzo[e]azulene (XXIII)

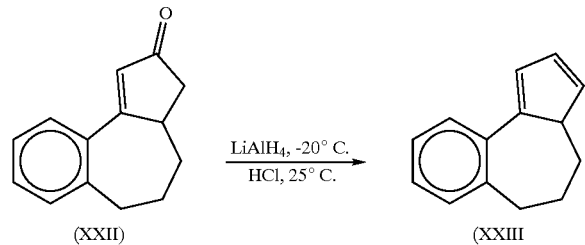

A solution of 2.2 g of the compound (XXII), prepared as described above, in 20 ml of ethyl ether, are charged, over a period of about 1 hour, into a 250 ml flask cooled to −20° C., containing a mixture of 2.1 g (55 mmoles) of LiAlH$_4$ and 100 ml of ethyl ether. A light yellow suspension is formed which is maintained under stirring at room temperature for a further 2 hours. At the end of the reaction, the suspension is carefully poured into water and ice and is then acidified with HCl and extracted with four 50 ml portions of ethyl ether. The organic phase is treated with p-toluenesulfonic acid in excess and maintained at 4° C. for 18 hours. It is then hydrolyzed with water saturated with NaHCO$_3$ and washed until neutrality. After drying on Na$_2$SO$_4$ and removing the solvent under vacuum, 1.1 g of the desired product (XXIII) are obtained in the form of a red oil.

2f) Synthesis of bis-(4,5,6-trihydro-benzo[e]azulenyl)-zirconium dichloride (XXIV)

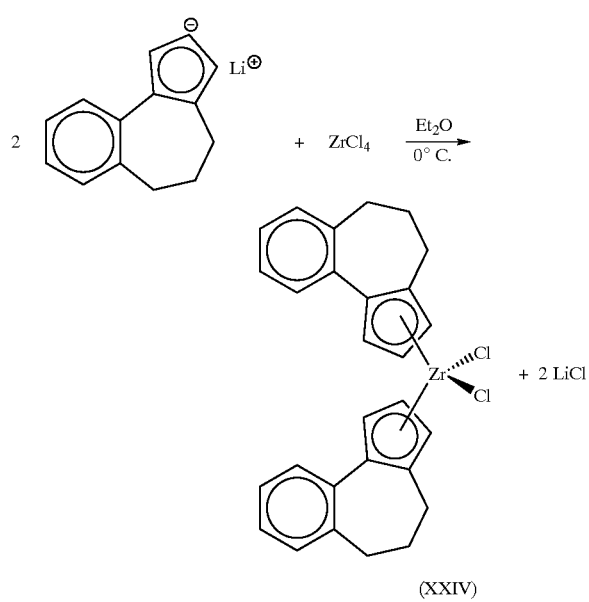

1.1 g (6 mmoles) of the product (XXIII), obtained as described above, are dissolved in ethyl ether in a 100 ml flask and 10 ml of lithium butyl 1.6 M in hexane (16 mmoles) are added, after cooling to −20° C., over a period of about 30 minutes. The mixture is then brought to room temperature and left to react, under stirring, for a further 4 hours. A light yellow solid is formed, which is recovered by filtration, washed three times with 10 ml of hexane and dried under vacuum.

0.94 g of lithium salt of compound (XXIII) are thus obtained (830 yield), which are charged into a 250 ml flask containing 100 ml of ethyl ether. The suspension thus obtained is cooled to 0° C., 0.52 g of ZrCl$_4$ are added and the mixture is maintained under stirring for 4 hours. The reaction mixture is brought to room temperature, filtered and the solid extracted three times with 10 ml of ethyl ether. After evaporating the ether, an orange oily residue is obtained which is treated under heat with a mixture of toluene/hexane (1/1 by volume). The red insoluble part is removed by filtration under heat and on cooling the hydrocarbon solution, a yellow-orange solid is formed, which is recovered by filtration, washed with hexane (10 ml) and dried under vacuum. 0.21 g of the desired zirconium complex (XXIV) are thus obtained.

$^1$H NMR (CDCl$_3$ δ, ppm rel. to TMS): 7.4–7.0 (m, 8H); 6.63 (t, 1H); 6.60 (t, 1H); 6.21 (m, 4H); 3.1–2.9 (m, 2H); 2.8–2.4 (m, 6H); 2.3–1.9 (m, 4H).

Example 3

Synthesis of bis-(7,9-di-methyl-4,5-di-hydro-benzo [d]indenyl)zirconium dichloride (XXX)

3a) Synthesis of 5,7-dimethyl-1-oxo-2-ethoxycarbonyl-1,2,3,4-tetrahydronaphthalene (XXV)

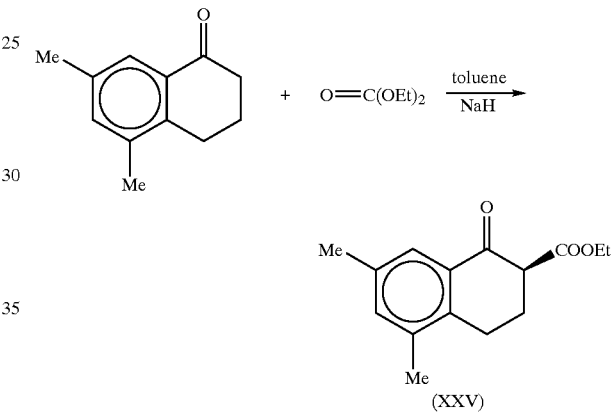

A suspension of 12.2 g (0.53 moles) of sodium hydride in a liter of toluene are maintained under stirring in a 2 liter flask for 2 hours at room temperature, and 85 ml (0.69 moles) of diethylcarbonate are then added. The mixture is heated to 90° C. and 25 g of 5,7-dimethyl-1-tetralone (0.14 moles) dissolved in 150 ml of toluene are added, in about 2 hours. The reaction mixture is kept under stirring for a further 8 hours at 90° C. until the reagent disappears. At the end the reaction mixture is hydrolyzed by pouring it into ice containing 50 ml of glacial acetic acid. The phases are separated and extracted repeatedly with ethyl ether, the overall organic phase is washed with water saturated with NaHCO$_3$, then with water until neutrality and finally dried on anhydrous Na$_2$SO$_4$. Upon removal of the solvents vents at reduced pressure, 33 g of the desired pure ketoester (XXV) are obtained in the form of a red oil (96% yield). NMR spectra show that the product is present in solution in ketone and enolic form in a ratio of 55% and 45% respectively.

$^1$H NMR (CDCl$_3$ δ, ppm rel. to TMS): 12.50 (s, 0.45H); 7.71 (s, 0.55H); 7.49 (s, 0.45H); 7.17 (s, 0.55H); 7.01 (s, 0.45H); 4.25 (dq, 2H); 3.53 (dd, 0.55H); 3.1–2.2 (m, 4H); 2.30 (s, 3H); 2.24 (s, 3H); 1.34 (t, 0.45×3H); 1.28 (t, 0.55×3H).

$^{13}$C NMR (CDCl$_3$ δ, ppm rel. to TMS): 194.38; 173.46; 170.96; 166.18; 136.77; 136.96; 136.63; 136.08; 135.44; 134.01; 132.66; 130.64; 129.81; 128.93; 97.07; 61.79;

61.11; 54.73; 26.43; 25.11; 24.23; 21.64; 21.47; 21.04; 19.89; 19.84; 15.04; 14.87.

3b) Synthesis of 5,7–1-oxo-2-ethoxycarbonyl-2-(prop-2-inyl)-1,2,3,4-tetrahydronaphthalene (XXVI)

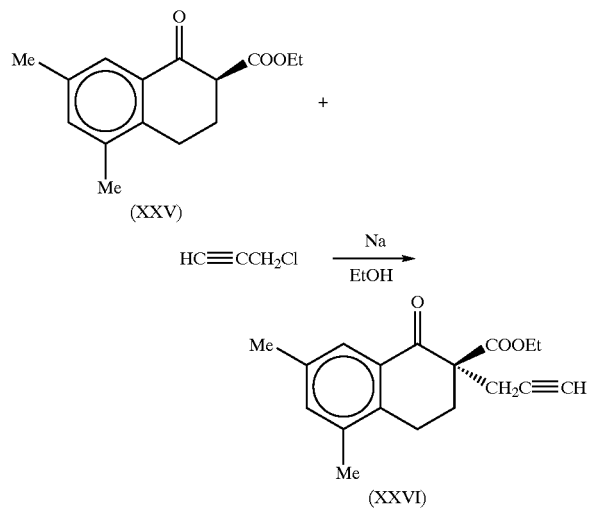

5.0 g (0.217 moles ) of metal sodium and 500 ml of anhydrous ethyl alcohol are charged into a 1 liter flask and kept under stirring until the complete dissolution of the sodium; the ketoester (XXV) is then added. 30 ml of propargyl chloride (0.285 moles) dissolved in 70 ml of toluene and 20 ml of EtOH are then added, by means of a filter funnel, over a period of 1 hour. The suspension thus obtained is maintained under stirring at reflux temperature for a further 8 hours, is then cooled to room temperature, hydrolyzed by the addition of water and extracted with various portions of ethyl ether. The organic phase is repeatedly washed with water until neutrality and dried on anhydrous $Na_2SO_4$. The solvent is subsequently evaporated under vacuum, thus obtaining 25 g of a red oil which, upon subsequent $^1H$ NMR analysis proves to be the desired product (XXVII) (65% yield).

$^1H$ NMR (CDCl$_3$ δ, ppm rel. to TMS): 7.72 (s, 1H); 7.19 (s, 1H); 4.13 (dq, 2H); 3.1–2.6 (m, 2H); 2.86 (dd, 2H); 2.5–2.2 (m, 2H); 2.31 (s, 3H), 2.24 (s, 3H); 2.01 (t, 1H); 1.14 (t, 3H).

3c) Synthesis of 5,7-dimethyl-1-oxo-2-ethoxycarbonyl-2-(2-oxo-propyl)-1,2,3,4-tetrahydronaphthalene (XXVII)

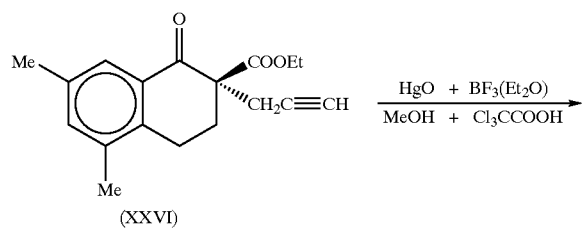

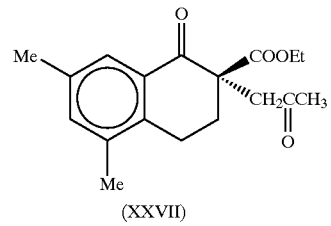

The following products are charged in order into a 1 liter flask: 1.5 g (7 mmoles) of HgO, 2 ml (15.7 mmoles) of boron trifluoride etherate (BF$_3$(Et$_2$O), 0.015 g (0.9 mmoles) of trichloroacetic acid, 400 ml of methanol and 20 g (0.07 moles) of the product (XXVI) obtained as described above. The reaction mixture is heated to 50° C. and maintained at this temperature, under stirring for 5 hours. After cooling to room temperature, water is added to hydrolyze the mixture, which is then extracted with various portions of ethyl ether. 19.3 g of an oily liquid are obtained from the organic phase, after anhydrifying on Na$_2$SO$_4$ and removal of the solvent at reduced pressure, which, after characterization, proves to be the desired product having formula (XXVII) (96% yield).

$^1H$ NMR (CDCl$_3$ δ, ppm rel. to TMS): 7.71 (s, 1H); 7.18 (s, 1H); 3.66 (s, 3H); 3.01 (s, 2H); 2.79 (m, 2H); 2.45 (m, 2H); 2.31 (s, 3H); 2.23 (s, 3H); 2.22 (s, 3H).

3d) Synthesis of 6,8-dimethyl-3,3a,4,5-tetrahydro-cyclopenta[a]naphthalen-2-one (XXVII)

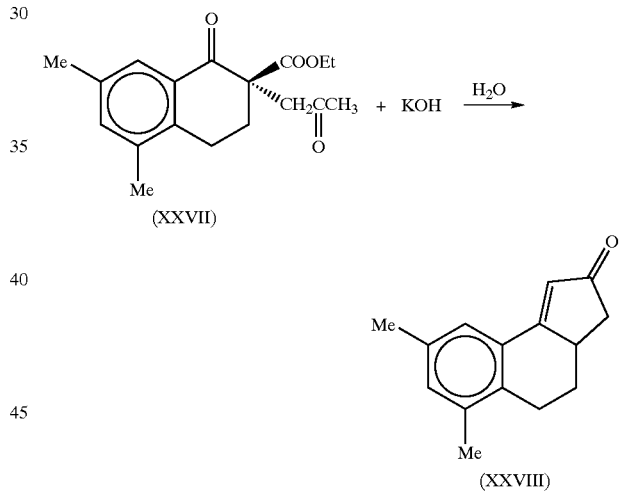

The following products are charged in order into a 500 ml flask: 250 ml of water, 30 g (0.53 moles) of potassium hydroxide and 10 g (34.7 mmoles) of the product having formula (XXVII) obtained as described above. The mixture is then heated to reflux temperature for 50 hours, the reaction trend being controlled by T.L.C. At the end, a suspension is obtained which is cooled to room temperature and extracted with various portions of ethyl ether, the overall organic phase is then washed with water saturated with NH$_4$Cl and subsequently with water until neutrality, and is finally dried on anhydrous Na$_2$SO$_4$. After removal of the solvent at reduced pressure, 3.5 g of brown semi-solid residue are obtained, which contains about 70% of the desired cyclopentenone product having formula (XXVIII) (33% yield) . The pure product is then recovered by means of flash chromatography, using a 70/30 (by volume) mixture of hexane/ethyl acetate as eluant and SiO$_2$ (Merck) 32–60 as stationary phase.

$^1$H NMR (CDCl$_3$ δ, ppm rel. to TMS): 7.31 (s, 1H); 7.08 (s, 1H); 6.35 (d, 1H); 3.1–2.6 (m, 4H); 2.4–2.1 (m, 2H); 2.32 (s, 3H); 2.24 (s, 3H); 1.8–1.5 (m, 1H).

$^{13}$C NMR (CDCl$_3$ δ, ppm rel. to TMS): 208.87; 176.97; 137.75; 136.42; 135.48; 134.50; 130.55; 125.82; 123.96; 108.24; 107.23; 43.44; 40.09; 30.46; 27.47; 21.53; 20.13.

3e) Synthesis of 6,8-dimethyl-3a,4,5-trihydrocyclopenta[a]naphthalene (XXIX)

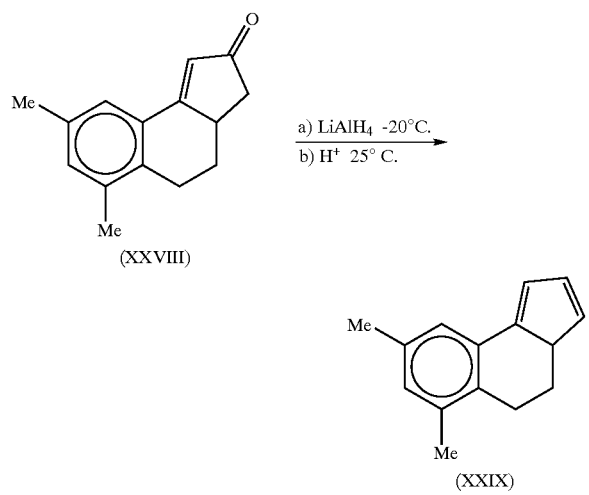

1.2 g (31 mmoles) of LiAlH$_4$ are suspended in 50 ml of diethyl ether in a 100 ml flask and, after bringing the temperature to –20° C., a solution of 1.6 g (7.5 mmoles) of the product having formula (XXX), obtained as described above, in 20 ml of Et$_2$O, are added over a period of about 30 minutes. At the end of the addition the temperature is brought to 25° C. and the mixture is maintained under stirring for a further 3 hours. The reaction mixture is then hydrolyzed by carefully pouring it into water and ice, is acidified by adding 5 ml of conc. HCl, extracted with ethyl ether and the organic phase is anhydrified on Na$_2$SO$_4$. After evaporation of the solvent under vacuum, 1.4 g of a light brown solid product are obtained, which, after characterization, proves to be the desired substituted cyclopentadiene product having formula (XXIX), almost pure.

3f) Synthesis of bis-(6,8-dimethyl-4,5-dihydrocyclopenta[a]naphthalenyl)zirconium dichloride (XXX)

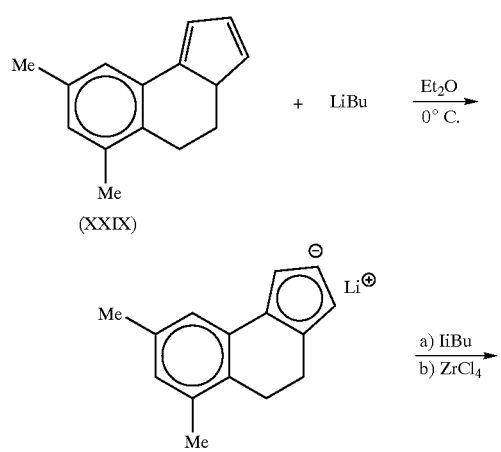

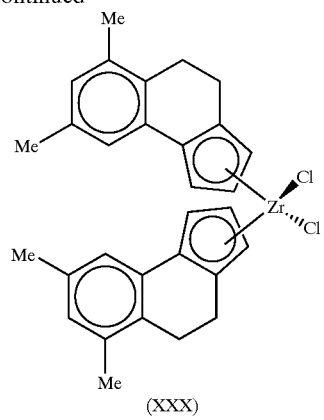

75 ml of ethyl ether and 1.4 g (6.6 mmoles) of the diene having formula (XXIX) obtained as described above, are charged into a 250 ml flask. After cooling the mixture to 0° C., 10 ml of a solution of lithium butyl 1.6 M in hexane (16 mmoles) are added by means of a syringe, the temperature is left to slowly rise to 25° C. and the mixture is maintained under stirring for 18 hours. The solvent is then removed at reduced pressure and hexane (100 ml) is added. The light brown solid which is formed in this phase is recovered by filtration, washed on a filter with 3 20 ml portions of hexane and dried under vacuum. 0.3 g of the lithium salt of the product having formula (XXIX) are thus obtained.

This lithium salt (1.48 mmoles) is suspended in 100 ml of anhydrous ethyl ether in a 250 ml flask and, after cooling to –20° C., 0.16 g (0.69 mmoles) of ZrCl$_4$ are added. The temperature is left to rise to 25° C. and the mixture is then kept under stirring for 4 hours. A light-coloured solid is formed which can be easily decanted. The suspension is filtered, the resulting ether solution is then dried and the solid thus obtained is re-crystallized from toluene/pentane. The desired metallocene complex having formula (XXX) is thus recovered.

Examples 4–14

Copolymerization of Ethylene with MAO as Co-catalyst

Examples 4 to 14 refer to a series of co- and ter-polymerization tests for the preparation of elastomeric polymers of the EP(D)M type based on ethylene/propylene/ethylidenenorbornene (ENB), carried out using a catalytic system comprising one of the metallocene complexes, obtained as described above in examples 1 and 2, and methylalumoxane (MAO) as cocatalyst. The specific polymerization conditions of each example and the results obtained are indicated in Table (II), which specifies in succession, the reference example number, the metallocene complex used, the quantity of zirconium used, the atomic ratio between aluminum in MAO and zirconium in the metallocene, the total polymerization pressure, the initial concentration of ENB, if present, the activity of the catalytic system as kilograms of polymer per gram of metal zirconium per hour (kg$_{pol.}$/g$_{Zr}$×h), the relative quantity, by weight, of the C$_3$ monomeric units and ENB in the polymer, the weight average molecular weight M$_w$ and the molecular weight dispersion M$_w$/M$_n$.

The polymerization is carried out in a 0.5 liter pressure reactor, equipped with a magnetic anchor drag stirrer and an external jacket connected to a heat exchanger for the temperature control. The reactor is previously flushed by maintaining under vacuum (0.1 Pascal) at a temperature of 80° C. for at least 2 h.

120 g of liquid "polymerization grade" propylene and the ENB diene, if required, are fed into the reactor at 23° C., in such a quantity as to obtain the molar concentration indicated in the corresponding column in table (II) below. The reactor is then brought to the polymerization temperature of 40° C. and, "polymerization grade" gaseous ethylene is fed by means of a plunged pipe until the total desired equilibrium pressure (2.0–2.7 MPa) is reached. Under these conditions the molar concentration of ethylene in the liquid phase ranges from 11 to 23%, depending on the total pressure of the system, as can be easily calculated using the appropriate liquid-vapor tables.

MAO, as a 1.5 M solution (as Al) in toluene and the desired quantity of one of the above metallocene complexes, as a toluene solution having a concentration generally ranging from $3\times10^{-4}$ to $1\times10^{-3}$ M, are charged into a suitable tailed test-tube, maintained under nitrogen. The catalyst solution thus formed is maintained at room temperature for a few minutes and is then transferred under a stream of inert gas to a metal container from which it is introduced into the reactor, by means of an overpressure of nitrogen.

The polymerization reaction is carried out at 40° C. care being taken that the total pressure is kept constant by continuously feeding ethylene to compensate the part which has reacted in the meantime. After 15 minutes the feeding of ethylene is interrupted and the polymerization is stopped by the rapid degassing of the residual monomers. The polymer is recovered, after washing it with ethyl alcohol and drying at 60° C., at a reduced pressure of 1000 Pa, for at least 8 hours, in order to completely eliminate any possible residual monomers. The solid thus obtained is weighed and the catalytic activity is calculated as described above. The content of the various $C_3$ monomeric units and ENB is measured on the dried and homogenized solid, by means of the known techniques based on IR spectroscopy, together with the weight ($M_w$) and number ($M_n$) average molecular weight. The results are indicated in Table II.

number, the quantity of zirconium used, the atomic ratio between aluminum and zirconium, the atomic ratio between boron and zirconium, the total polymerization pressure, the activity of the catalytic system with reference to the zirconium, the relative quantity, by weight, of the $C_3$ monomeric units in the polymer, the weight average molecular weight $M_w$ and the molecular weight dispersion $M_w/M_n$.

Preparation of the Catalytic System

Al(iso-Bu)$_3$ as a 0.4 M solution in toluene and the desired quantity of the metallocene complex (XVIII), as a toluene solution having a concentration generally ranging from $3\times10^{-4}$ to $1\times10^{-3}$ M, are charged into a suitable tailed test-tube, maintained under nitrogen. The solution thus formed is maintained under stirring at 23° C. for 15 minutes, after which a toluene solution, having a concentration generally ranging from $5\times10^{-4}$ to $1\times10^{-3}$ M, of [CPh$_3$][B(C$_6$F$_5$)$_4$] is added, and then, after a few minutes, is transferred under a stream of inert gas to a metal container from which it is introduced into the reactor, by means of an overpressure of nitrogen.

Polymerization

The polymerization is carried out in a 0.5 liter pressure reactor, equipped with a magnetic anchor drag stirrer and an external jacket connected to a heat exchanger for the temperature control. The reactor is previously flushed by maintaining under vacuum (0.1 Pascal) at a temperature of 80° C. for at least 2 h.

120 g of liquid "polymerization grade" propylene and the exact quantity of Al(iso-Bu)$_3$ so as to obtain an aluminum concentration of $5\times10^{-3}$ moles/liter, are fed into the reactor at 23° C. The reactor is then brought to the polymerization temperature of 40° C. and, "polymerization grade" gaseous ethylene is fed by means of a plunged pipe until the desired equilibrium pressure (2.2–2.7 MPa) is reached. Under these conditions the molar concentration of ethylene in the liquid phase ranges from 12 to 23%, depending on the total pressure of the system, as can be easily calculated using the appropriate liquid-vapor tables. At this point the catalytic

TABLE II ethylene co- and ter-polymerization according to examples 4 to 14

| Example Nr. | Complex (formula) | Zr (moles $\times$ 10$^6$) | Al/Zr (mol./mol.) | P$_{total}$ (MPa) | ENB$_{initial}$ (% moles) | Activity (kg$_{pol}$/g$_{Zr}$xh) | C$_{3\ (polymer)}$ (weight %) | ENB$_{(polymer)}$ (weight %) | M$_w$ ($\times 10^3$) | M$_w$/M$_n$ |
|---|---|---|---|---|---|---|---|---|---|---|
| 4 | (XVIII) | 0.40 | 3950 | 2.5 | — | 3360 | 34.5 | — | 378 | 3.1 |
| 5 | (XVIII) | 0.53 | 3600 | 2.2 | — | 912 | 53.3 | — | 131 | 3.0 |
| 6 | (XVIII) | 0.66 | 2350 | 2.5 | 0.4 | 1299 | 45.9 | 3.5 | 105 | 2.9 |
| 7 | (XVIII) | 0.27 | 5850 | 2.5 | — | 4721 | 38.5 | — | 160 | 3.8 |
| 8 | (XVIII) | 1.06 | 2230 | 2.5 | 0.8 | 1120 | 38.4 | 3.7 | 166 | 2.5 |
| 9 | (XVIII) | 0.20 | 7900 | 2.7 | — | 10769 | 36.3 | — | 229 | 3.0 |
| 10 | (XVIII) | 1.33 | 2200 | 2.7 | 1.2 | 793 | 33.4 | 4.9 | 218 | 2.7 |
| 11 | (XXIV) | 0.31 | 4950 | 2.5 | — | 1560 | 31.0 | — | 148 | 2.7 |
| 12 | (XXIV) | 0.43 | 3580 | 2.7 | — | 1533 | 28.3 | — | 362 | 2.9 |
| 13 | (XXIV) | 1.55 | 1990 | 2.2 | — | 1191 | 37.3 | — | 243 | 3.1 |
| 14 | (XXIV) | 0.93 | 3310 | 2.4 | — | 1134 | 31.8 | — | 138 | 2.8 |

Examples 15 to 19

Examples 15 to 19 refer to copolymerization tests of ethylene with propylene for the preparation of the corresponding elastomeric polymers of the EPR type, carried out using a catalytic system comprising the metallocene complex having formula (XVIII) obtained as described above in example 1, an aluminum alkyl and an appropriate compound of boron as co-catalyst (catalytic system of the cationic type). The specific polymerization conditions of each example and the results obtained are indicated in Table III, which specifies in succession, the reference example system is introduced from a suitable container connected to the reactor, by means of an overpressure of nitrogen. The polymerization reaction is carried out using the same procedure and under the same conditions as the previous examples 4 to 14. At the end, the polymer thus obtained is weighed and the catalytic activity is calculated as kilograms of polymer per gram of metal zirconium per hour (kg$_{pol}$/g$_{Zr}$xh). The content of propylene units is measured on the dried and homogenized solid, by means of the known techniques based on IR spectroscopy, together with the weight ($M_w$) and number ($M_n$) average molecular weight. The results are indicated in Table (III).

TABLE III

| | Ethylene co-polymerization according to examples 15 to 19 | | | | | | | |
|---|---|---|---|---|---|---|---|---|
| Example Nr. | Zr (moles × $10^6$) | Al/Zr (mol/ mol) | B/Zr (mol/ mol) | $P_{total}$ (MPa) | Activity ($kg_{pol}/g_{Zr}$×h) | $C_{3\ (polymer)}$ (weight %) | $M_w$ (×$10^3$) | $M_w/M_n$ |
| 15 | 0.38 | 316 | 1.1 | 2.2 | 1157 | 40.4 | 180 | 3.4 |
| 16 | 0.38 | 316 | 1.1 | 2.5 | 1619 | 35.5 | 281 | 3.3 |
| 17 | 0.38 | 316 | 4.3 | 2.2 | 1215 | 44.3 | 186 | 2.5 |
| 18 | 0.38 | 316 | 2.1 | 2.5 | 1677 | 36.3 | 215 | 2.9 |
| 19 | 0.38 | 316 | 4.3 | 2.5 | 1735 | 37.2 | 214 | 2.6 |

What is claimed is:

1. A polycyclic cyclopentadienyl compound having the following formula (II):

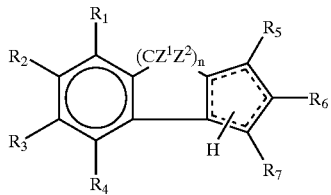

(II)

wherein each of $R^1$, $R^2$, $R^3$, $R^4$, $R^5$, $R^6$, $R^7$, $Z^1$ and $Z^2$ independently represents hydrogen or an organic substituent having from 1 to 15 carbon atoms, and one of said R or Z groups can be a divalent organic group further bound to another organic group having from 5 to 20 carbon atoms and comprising a cyclopentadienyl group, and n has any of the integer values from 1 to 10;

or a mixture of compounds of formula (II).

2. The polycyclic compound according to claim 1, wherein each of $R^1$, $R^2$, $R^3$, $R^4$, $R_5$, $R^6$, $R^7$, $Z^1$ and $Z^2$ represents hydrogen or an alkyl group, linear or branched, having from 1 to 6 carbon atoms, and n has values of from 1 to 3.

3. The polycyclic compound according to claim 1, wherein $Z^1$ and $Z^2$ are both hydrogen.

4. The polycyclic compound according to claim 3, wherein any two of $R_1$, $R_2$, $R_3$ and $R_4$ are linear or branched alkyl having from 1 to 4 carbon atoms.

5. The polycyclic compound according to claim 1, wherein $R_1$, $R_2$, $R_3$, $R_4$, $Z^1$ and $Z^2$ each represent hydrogen and at least one of $R_5$, $R_6$, or $R_7$, independently represent methyl or ethyl.

6. The polycyclic compound according to claim 1, wherein one of $R_5$, $R_6$ or $R_7$, is a divalent hydrocarbon or silane group having from 2 to 6 carbon atoms, further bound to a second cyclopentadienyl group having from 5 to 20 carbon atoms.

7. The compound according to claim 5, wherein at least one of $R^5$, $R^6$ or $R^7$ represents methyl.

8. The compound according to claim 6, wherein $R_5$ or $R_7$ is a divalent hydrocarbon or silane group having from 2 to 6 carbon atoms.

9. The compound according to claim 6, wherein the second cyclopentadienyl group is cyclopentadienyl, indenyl, fluorenyl or a derivative thereof.

* * * * *